US00PP15978P2

(12) United States Plant Patent
van Rijn

(10) Patent No.: US PP15,978 P2
(45) Date of Patent: Sep. 20, 2005

(54) ***ANTHURIUM* PLANT NAMED 'RIJN200142'**

(50) Latin Name: *Anthurium andreanum*
Varietal Denomination: Rijn200142

(75) Inventor: Leonardus W. B. M. van Rijn, De Lier (NL)

(73) Assignee: RijnPlant B.V., Schipluiden (NL)

( * ) Notice: Subject to any disclaimer, the term of this patent is extended or adjusted under 35 U.S.C. 154(b) by 26 days.

(21) Appl. No.: 10/917,154

(22) Filed: Aug. 12, 2004

(51) Int. Cl.[7] ..... A01H 5/00

(52) U.S. Cl. ..... Plt./365

(58) Field of Search ..... Plt./365

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Anthurium* plant named 'Rijn200142', characterized by its upright and outwardly spreading plant habit; freely clumping growth habit; relatively small, durable and dark green-colored leaves; red-colored spathes with yellow-colored spadices that are positioned above and beyond the foliage on strong and erect scapes; freely flowering habit; and good inflorescence longevity.

1 Drawing Sheet

Botanical classification/cultivar designation: *Anthurium andreanum* cultivar Rijn200142.

BACKGROUND OF THE INVENTION

The present invention relates to a new and distinct cultivar of *Anthurium* plant, botanically known as *Anthurium andreanum*, and hereinafter referred to by the name 'Rijn200142'.

The new *Anthurium* is a product of a planned breeding program conducted by the Inventor in De Lier, The Netherlands. The objective of the program is to create and develop new compact, freely clumping and freely flowering *Anthurium* cultivars with strong roots, dark green-colored leaves, attractive spathe color and good inflorescence longevity.

The new *Anthurium* originated from a cross by the Inventor on Aug. 19, 1999 of a proprietary selection of *Anthurium andreanum* identified as code number 9613, not patented, as the female, or seed, parent with a proprietary selection of *Anthurium andreanum* identified as code number 9513, not patented, as the male, or pollen, parent. The cultivar Rijn200142 was discovered and selected by the Inventor as a flowering plant within the progeny of the stated cross in a controlled environment in De Lier, The Netherlands in, July, 2001.

Asexual propagation of the new cultivar by meristem culture in a laboratory in Belgium since November, 2001, has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Rijn200142. These characteristics in combination distinguish 'Rijn200142' as a new and distinct cultivar:

1. Upright and outwardly spreading plant habit.
2. Freely clumping growth habit.
3. Relatively small, durable and dark green-colored leaves.
4. Red and green-colored spathes with yellow-colored spadices that are positioned above and beyond the foliage on strong and erect scapes.
5. Freely flowering habit.
6. Good inflorescence longevity.

Plants of the new *Anthurium* can be compared to plants of the female parent, the proprietary selection identified as code number 9613. In side-by-side comparisons conducted in De Lier, The Netherlands, plants of the new *Anthurium* differed from plants of the selection 9613 in the following characteristics:

1. Plants of the new *Anthurium* had thicker leaves than plants of the selection 9613.
2. Plants of the new *Anthurium* had thicker spathes than plants of the selection 9613.
3. Plants of the new *Anthurium* and the selection 9613 differed in spathe coloration as plants of the selection 9613 had solid red-colored spathes.

Plants of the new *Anthurium* can be compared to plants of the male parent, the selection 9513. In side-by-side comparisons conducted in De Lier, The Netherlands, plants of the new *Anthurium* differed from plants of the selection 9513 primarily in spathe coloration as plants of the selection 9513 had orange-colored spathes.

Plants of the new *Anthurium* can be compared to plants of the cultivar Red Love, disclosed in U.S. Plant Pat. No. 11,005. In side-by-side comparisons conducted in De Lier, The Netherlands, plants of the new *Anthurium* differed from plants of the cultivar Red Love in the following characteristics:

1. Plants of the new *Anthurium* had thicker leaves than plants of the cultivar Red Love.
2. Plants of the new *Anthurium* had thicker spathes than plants of the cultivar Red Love.

3. Plants of the new *Anthurium* and the cultivar Red Love differed in spathe coloration as plants of the cultivar Red Love had solid red-colored spathes.

BRIEF DESCRIPTION OF THE PHOTOGRAPH

The accompanying colored photograph illustrates the overall appearance of the new *Anthurium*, showing the colors as true as it is reasonably possible to obtain in colored reproductions of this type. Colors in the photograph may differ slightly from the color values cited in the detailed botanical description which accurately describe the colors of the new *Anthurium*.

The photograph comprises a top perspective view of a typical flowering plant of the cultivar Rijn200142.

DETAILED BOTANICAL DESCRIPTION

In the following description, color references are made to The Royal Horticultural Society Colour Chart, 2001 Edition, except where general terms of ordinary dictionary significance are used. The aforementioned photograph and the following observations and measurements describe 19-month old plants grown in 14-cm containers in De Lier, The Netherlands, during the spring in a glass-covered greenhouse with average day temperatures of 23° C., average night temperatures of 21° C. and light levels about 6 kilolux.

Botanical classification: *Anthurium andreanum* cultivar Rijn200142.

Parentage:

*Female parent.*—Proprietary selection of *Anthurium andreanum* identified as code number 9613, not patented.

*Male parent.*—Proprietary selection of *Anthurium andreanum* identified as code number 9513, not patented.

Propagation:

*Method.*—By meristem culture.

*Time to initiate roots on a meristem-cultured plant.*—About four weeks at 20 to 24° C.

*Time to develop roots on a meristem-cultured plant.*—About nine months at 20 to 24° C.

*Root description.*—Thick, fleshy, dark pink to cream-colored; lateral roots, thick and abundant.

Plant description:

*Plant shape.*—Upright and outwardly spreading plant habit, narrow inverted triangle, symmetrical.

*Growth habit.*—Freely clumping, bushy and dense growth habit; about nine clumps per plant; moderately vigorous.

*Plant height, from soil level to top of leaf plane.*—About 37 cm.

*Plant height, from soil level to top of inflorescences.*—About 50 cm.

*Plant diameter or spread.*—About 57 cm.

*Foliage description.*—Arrangement: Alternate; simple. Length: About 15.7 cm. Width: About 9.2 cm. Shape: Deltoid. Apex: Apiculate. Base: Cordate. Margin: Entire; undulate. Texture, upper and lower surfaces: Leathery; glabrous, smooth; durable. Venation pattern: Pinnate. Color: Developing leaves, upper and lower surfaces: Slightly darker than between 152A and N199A. Fully developed leaves, upper surface: Darker than between 139A and 147A. Fully developed leaves, lower surface: 146A to 147B. Venation, upper surface: 143A. Venation, lower surface: 144B. Petiole: Length: About 26.8 cm. Diameter, just below geniculum: About 4 mm. Diameter, at plant base: About 6 mm. Texture, upper and lower surfaces: Smooth, glabrous; slightly glossy. Color, upper surface: 143A. Color, lower surface: 143B. Geniculum length: About 1.8 cm. Geniculum diameter: About 5 mm. Geniculum color: 144A. Wing length: About 4.7 cm. Wing diameter: About 5 mm. Wing color: 146A to 146B.

Inflorescence description:

*Inflorescence arrangement.*—Spathes with spadices held above and beyond the foliage. Flowering structures arise from leaf axils. Freely and continuous flowering during the autumn in De Lier, The Netherlands. Typically about nine inflorescences per plant. Inflorescences not fragrant.

*Inflorescence longevity.*—Inflorescences last about two months under winter conditions and about three months under summer conditions; inflorescences persistent.

*Spathe.*—Length: About 7.6 cm. Width: About 7.1 cm. Shape: Reniform. Apex: Abruptly acute. Base: Obtuse. Margin: Entire. Texture, upper and lower surfaces: Leathery; glabrous, smooth. Aspect: Cupped; about 15° from vertical. Color: When developing, front surface: 47A; towards the basal margins, 146C. When developing, rear surface: 47B to 47C; towards the basal margins, 146C to 146D. Fully developed, front surface: 46B to 47A; towards the basal margins, more green than 147A. With development, 46A; towards the basal margins, darker than 141A. Fully opened, rear surface: 48A; towards the basal margins, 146A to 146B.

*Spadix.*—Length: About 4.9 cm. Diameter: About 7 mm. Shape: Columnar, tapering towards the apex; apex, obtuse; base, obtuse. Cross section: Rounded. Aspect: About 3° from vertical. Color: Immature: Initially, 144A; then closer to 14B. Mature: 11D; towards the base, 13B.

*Flowers.*—Quantity per spadix: Numerous, about 200. Shape: Rounded. Height: About 0.5 mm. Diameter: About 1.5 mm.

*Reproductive organs.*—Androecium: Anther color: 11D. Amount of pollen: Scarce. Pollen color: 11C. Gynoecium: Stigma shape: Ovoid. Stigma color: 155D. Ovary color: 155D.

*Scape.*—Length: About 35 cm. Diameter: About 4.5 mm. Strength: Strong. Aspect: Erect to slightly outwardly slanted to about 10° from vertical. Color: Towards the base, 143A; towards the apex, 175A.

*Seed and fruit.*—Seed and fruit development has not been observed on plants of the new *Anthurium*.

Disease/pest resistance: Under commercial production conditions, plants of the new *Anthurium* have not been observed to be resistant to pathogens or pests common to *Anthurium*.

Temperature tolerance: Plants of the new *Anthurium* have been observed to tolerate temperatures from about 14 to about 35 to 36° C.

It is claimed:

1. A new and distinct cultivar of *Anthurium* plant named 'Rijn200142', as illustrated and described.

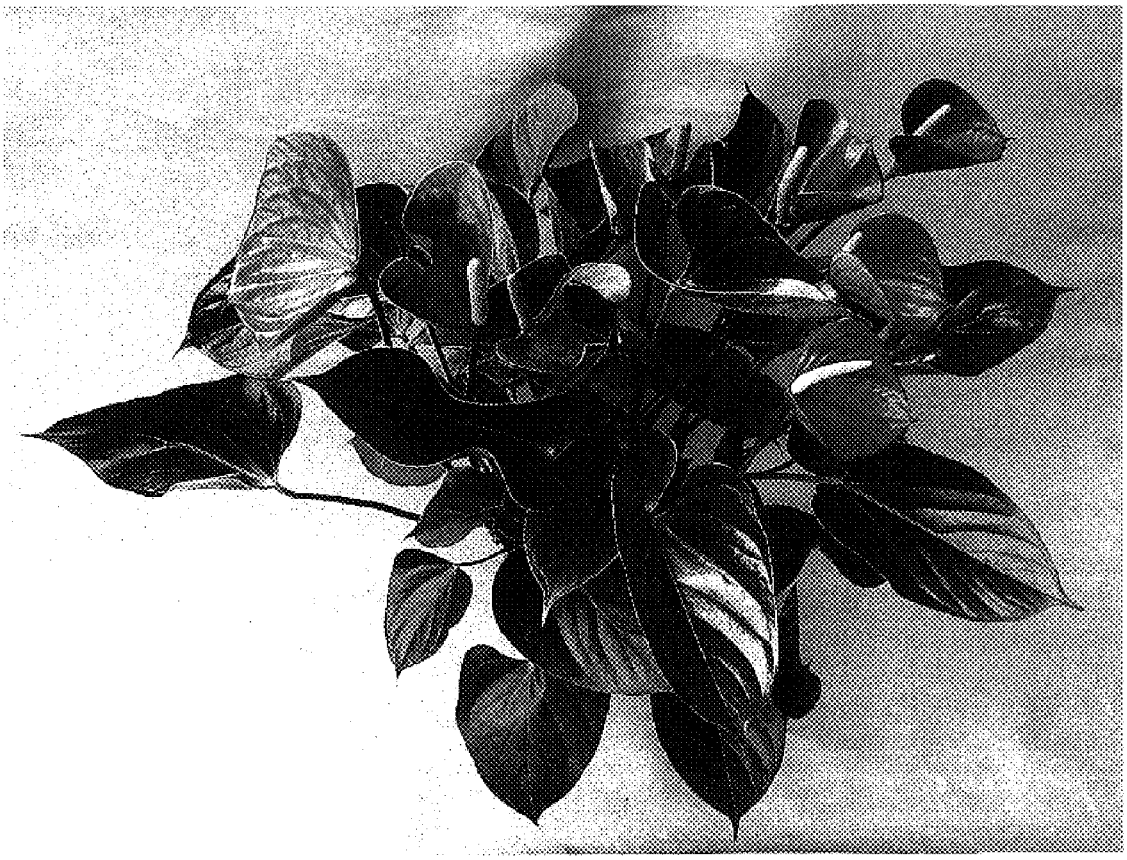

* * * * *